(12) United States Patent
Jiang et al.

(10) Patent No.: US 9,890,099 B2
(45) Date of Patent: Feb. 13, 2018

(54) NEUTRALIZATION OF ACIDIC CATALYSTS IN THE PRODUCTION OF PHENOL

(71) Applicant: Dow Global Technologies LLC, Midland, MI (US)

(72) Inventors: Xin Jiang, Shanghai (CN); Jianhai Mu, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/304,698

(22) PCT Filed: Apr. 23, 2014

(86) PCT No.: PCT/CN2014/076034
§ 371 (c)(1),
(2) Date: Oct. 17, 2016

(87) PCT Pub. No.: WO2015/161466
PCT Pub. Date: Oct. 29, 2015

(65) Prior Publication Data
US 2017/0036979 A1    Feb. 9, 2017

(51) Int. Cl.
| | | |
|---|---|---|
| *C07C 45/53* | (2006.01) | |
| *C07C 37/08* | (2006.01) | |
| *C07C 407/00* | (2006.01) | |
| *C07C 37/86* | (2006.01) | |
| *B01J 27/053* | (2006.01) | |

(52) U.S. Cl.
CPC ............ *C07C 37/08* (2013.01); *B01J 27/053* (2013.01); *C07C 37/86* (2013.01); *C07C 45/53* (2013.01); *C07C 407/00* (2013.01); *C07C 2601/14* (2017.05); *Y02P 20/52* (2015.11)

(58) Field of Classification Search
CPC ........ C07C 37/08; C07C 45/53; C07C 407/00
USPC ................................. 568/347, 798
See application file for complete search history.

(56) References Cited

U.S. PATENT DOCUMENTS

| 3,437,696 A | 4/1969 | Achard |
|---|---|---|
| 6,201,157 B1 * | 3/2001 | Keenan ................. C07C 37/08 |
| | | 568/311 |
| RE40,668 E | 3/2009 | Zakoshansky |

FOREIGN PATENT DOCUMENTS

| WO | 2001051439 A1 | 7/2001 |
|---|---|---|
| WO | 2012036826 A2 | 3/2012 |
| WO | 2012036827 A1 | 3/2012 |

* cited by examiner

*Primary Examiner* — Sikarl Witherspoon

(57) ABSTRACT

An improved method for the production of phenol. The method comprises (a) synthesizing phenol through a process that utilizes an acidic catalyst; (b) neutralizing the acidic catalyst after substantial completion of step (a) by addition thereto of a neutralization composition, wherein the neutralization composition contains an ethyleneamine derivative.

1 Claim, No Drawings

NEUTRALIZATION OF ACIDIC CATALYSTS IN THE PRODUCTION OF PHENOL

FIELD

This invention relates generally to an improved method for the production of phenol.

BACKGROUND

A commonly used phenol production method is decomposition of cumene hydroperoxide to phenol, acetone, and α-methylstyrene in the presence of an acidic catalyst. Another method to produce phenol is oxidizing at least a portion of a feed comprising cyclohexylbenzene to produce an oxidation composition comprising cyclohexyl-1-phenyl-1-hydroperoxide. The oxidation composition may then be cleaved in the presence of an acidic catalyst to produce a cleavage reaction mixture comprising the acidic catalyst, phenol and cyclohexanone.

Typically, the acidic catalyst used in the phenol production processes is a strong, and comparably low corrosive inorganic acid, such as sulfuric or phosphoric acid. The acidic catalyst must be removed or neutralized to prevent further, undesired reactions in the downstream purification steps that produce phenol and other products. Commercial processes for the manufacture of phenol use inorganic bases, ion exchange resins, organic amines or a combination thereof to remove acidity from crude product stream.

The use of a strong base, such as sodium hydroxide or potassium hydroxide to neutralize the acidic catalyst is not desirable because it is difficult to achieve accurate pH control in a neutralization reaction between a strong acid and a strong base. Moreover, metal hydroxides generate salts that have a propensity to deposit on heat exchange surfaces, causing fouling and decreasing efficiency. Since ion exchange resins are temperature sensitive, the crude product stream must be cooled substantially prior to contact with the resin. The need to cool the product stream increases energy costs significantly because the crude product stream must then be re-heated prior to downstream purification operations. A further drawback of ion exchange resins is that they must be regenerated frequently, a labor-intensive and costly process which also results in formation of large amounts of aqueous waste. Moreover, ion exchange resins give a highly variable final pH in the crude produce stream, adversely affecting final product yields, and can also release alkali salts which cause fouling of equipment. Organic amines like methylpentamethyenediamine (MPMD) and hexamethylene (HMDA) are commonly used as neutralizers, but their neutralization efficiency is not good enough.

The problem addressed by this invention is the provision of an improved method for the production of phenol, that avoids or mitigates the foregoing neutralization problems.

STATEMENT OF INVENTION

We have now found that in the manufacture of phenol, neutralization of the acidic catalyst can be effected by the addition of an ethyleneamine compound after substantial completion of the decomposition reaction. Advantageously, the inventive process allows for neutralization of phenol product streams at elevated temperatures with minimal formation of byproducts, higher neutralization efficiency and no or minimal fouling caused.

Therefore, there is provided a method for the production of phenol, the method comprising: (a) synthesizing phenol through a process that utilizes an acidic catalyst; (b) neutralizing the acidic catalyst after substantial completion of step (a) by addition thereto of a neutralization composition, wherein the neutralization composition contains an ethyleneamine derivative.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As used herein, unless otherwise indicated, the phrase "molecular weight" refers to the number average molecular weight as measured in conventional manner.

The ethyleneamine derivative used in the invention functions to neutralize residual acidic catalyst in phenol product streams, resulting in minimal formation of byproducts, higher neutralization efficiency, and no or minimal fouling. The ethyleneamine is further advantageous because it can be used at elevated temperature, thus eliminating the need to cool the process stream (in those processes that use elevated temperature) prior to neutralization and then reheating prior to performing purification steps.

Ethyleneamine derivatives for use in the method of the invention are generally amine compounds having at least one ethyleneamine unit or repeating ethyleneamine units. An ethyleneamine unit is —(CR2-CR2-NH—)— where R is H or an alkyl (straight, branched or cyclic) group, preferably H. If R is alkyl, it is preferably C1-C10 alkyl, more preferably C1-C6 alkyl. Ethyleneamines have at least two amine groups, which groups are primary or secondary amine groups; tertiary amine groups are optionally also present. Ethyleneamine derivatives are commercially available, for instance from The Dow Chemical Company, or they may be prepared by those skilled in the art using literature methods.

In some embodiments of the invention, the ethyleneamine derivative is ethylenediamine (EDA), diethylenetriamine (DETA), triethylenetetramine (TETA) aminoethylpiperazine (AEP), tetraethylenepentamine (TEPA), Heavy Polyamine X (HPA X), or a mixture of two or more thereof. As is understood by those skilled in the art, Heavy Polyamine X is a complex mixture of linear, branched, and cyclic ethyleneamines. The structures of the principle components contain six or more nitrogen atoms per molecule. Its molecular weight is about 275. The product is commercially available from Dow.

In some embodiments, the ethyleneamine derivative is ethylenediamine, diethylenetriamine, triethylenetetramine, aminoethylpiperazine, or mixtures thereof. In some embodiments, the ethyleneamine derivative is ethylenediamine.

In some embodiments, the neutralization composition may contain other amines besides ethyleneamines, such as methylpentamethyenediamine (MPMD) and hexamethylenediamine (HMDA).

In some embodiments, the neutralization composition is substantially free of neutralizers other than ethyleneamines, such as caustic exchange resin, ammonia or ammonium hydroxide, basic clay, activated carbon, and anionic exchange resin. In some embodiments, the neutralization composition is substantially free of organic amines other than ethyleneamines. In some embodiments, the neutralization composition is substantially free of piperazine. By "substantially free" is meant that the neutralization composition contains less than 10 weight percent, alternatively less than 5 weight percent, alternatively less than 1 weight percent, or alternatively 0 weight percent, of such other neutralizers or amines, based on the total weight of the neutralization composition.

The synthesis step (a) of the method of the invention may be any known phenol synthesis process that utilizes an acidic catalyst. Such syntheses are known to those skilled in the art. In some embodiments, the synthesis comprises decomposing cumene hydroperoxide in the presence of an acidic catalyst to form phenol, acetone, and α-methylstyrene. In this process, the cumene hydroperoxide is typically decomposed at an elevated temperature, such as from about 30 to about 180 degrees Celsius, alternatively from about 60 to about 160 degrees Celsius, or alternatively from about 120 to about 160 degrees Celsius.

In some embodiments, the synthesis comprises (i) oxidizing at least a portion of a feed containing cyclohexylbenzene to produce an oxidation composition containing cyclohexyl-1-phenyl-1-hydroperoxide; and (ii) cleaving the oxidation composition in the presence of an acidic catalyst to produce a cleavage reaction mixture comprising the acidic catalyst, phenol, and cyclohexanone.

Examples of acidic catalysts typically used in phenol production include the substituents having a pKa value in aqueous media of less than about 5, such as the acid form of carboxylate, nitrates, phosphates, phosphonates, sulfates and sulfonates. A more specific example includes, but is not limited to, sulfuric acid.

In the invention, the neutralization composition is typically added to the reaction mixture containing the phenol product and residual acidic catalyst after substantial completion (e.g., at least 70 percent completion) of the phenol synthesis reaction but prior to purification steps. Percent completion may be measured as the weight percent consumption of the material being converted into phenol, such as cumene hydroperoxide or cyclohexyl-1-phenyl-1-hydroperoxide. The neutralization composition may be added at the elevated temperature of the phenol synthesis mixture, and there is no general requirement to cool the mixture prior to addition of the neutralization composition. Such temperatures may include, for instance, from room temperature to 70 degrees Celsius, alternatively from 30 to 50 degrees Celsius.

Typically a sufficient amount of the neutralization composition is added such that the residual acidic catalyst is neutralized, preferably fully neutralized. By way of example, such amount may include, for instance, from 20 ppm to 500 ppm based on total treated crude phenol.

Following neutralization of the acidic catalyst, the phenol may be isolated and/or purified by conventional techniques.

Some embodiments of the invention will now be described in detail in the following Examples.

Examples

1. Materials

A list of the materials used, their source, and purity as applicable are given in Table 1. All materials were used as received, with no further purification. All formulations were prepared gravimetrically.

TABLE 1

Materials Used in the Experiments

| Ingredient | Description | Source | Purity % |
|---|---|---|---|
| MEA | Monoethanolamine | Dow | >99.5 |
| DEA | Diethanolamine | Dow | >99.0 |
| NMEA | N-Methylethanolamine | Dow | >96.0 |

TABLE 1-continued

Materials Used in the Experiments

| Ingredient | Description | Source | Purity % |
|---|---|---|---|
| MIPA | Monoisopropanolamine | Dow | >99.0 |
| EDA | Ethylenediamine | Dow | >99.5 |
| DETA | Diethylenetriamine | Dow | >98.5 |
| TETA | Triethylenetetramine | Dow | >95.0 |
| AEP | Aminoethylpiperazine | Dow | >98.0 |
| AEEA | Aminoethylethanolamine | Dow | >99.5 |
| TEPA | Tetraethylenepentamine | Dow | >95.0 |
| HPA-X | Heavy Polyamine X | Dow | / |
| HMDA | Hexamethylene Diamine | Sinopharm Chemical Reagent Co., Ltd | >99.0 |
| MPMD | 2-Methylpentamethylenediamine | TCI | >98.0 |
| Crude Phenol | Mixture of phenol, acetone and impurities | One phenol producer | / |

2. Test Method—Neutralization Efficiency Test

The acid removal efficiency test was carried out in 50 g of crude phenol from one phenol producer. The matrix was dosed with 300 ppm $H_2SO_4$ to obtain the desired concentration for lab tests.

Selected amines were added into the matrix at a concentration of 300 ppm. The neutralization reactions were carried out at 38° C. for 2 mins. The acid removal efficiency was determined as acidity by the Metrohm autotitrater. The lower acidity means the better neutralization efficiency of amine. HMDA and MPMD are comparable examples.

3. Examples

Neutralization Efficiency

The neutralization efficiency of HMDA, MPMD and other amines in real crude phenol is tested. The acidity of crude phenol before and after adding 300 ppm $H_2SO_4$ is 119 mg KOH/g and 299.9 mg KOH/g respectively. 300 ppm $H_2SO_4$ and 300 ppm amine were added in the crude phenol base and heated for two mins.

EDA shows the best neutralization efficiency among the samples, followed by TETA, DETA, AEEA, HPA-X, TEPA, AEP, HMDA/MPMD, MEA, MIPA, NMEA and DEA. EDA, TETA and DETA are good candidates as they have better neutralization efficiency than benchmark HMDA and MPMD. Thus, it is possible to reduce total dosage level of amine in production if using DETA or TETA to replace HMDA/MPMD.

The neutralization efficiency of the comparable and inventive examples is summarized in Table 2. The inventive examples like EDA, TETA, DETA, AEEA, HPA-X, TEPA and AEP show higher neutralization efficiency than comparable examples HMDA and MPMD.

TABLE 2

Crude Phenol Composition

| Examples | Neutralizing Agent | Final Acidity mg/KOH g | Neutralization Efficiency |
|---|---|---|---|
| Comparable example | HMDA | 151.3 | Low |
| Comparable example | MPMD | 148.4 | Low |
| Comparable example | MEA | 160.8 | Low |

TABLE 2-continued

Crude Phenol Composition

| Examples | Neutralizing Agent | Final Acidity mg/KOH g | Neutralization Efficiency |
|---|---|---|---|
| Comparable example | MIPA | 178.1 | Low |
| Comparable example | NMEA | 187.7 | Low |
| Comparable example | DEA | 219.4 | Low |
| Inventive example | EDA | 37.6 | High |
| Inventive example | DETA | 99.6 | High |
| Inventive example | TETA | 70.6 | High |
| Inventive example | AEEA | 104.1 | Medium |
| Inventive example | HPA-X | 119.0 | Medium |
| Inventive example | TEPA | 125.6 | Medium |
| Inventive example | AEP | 133.9 | Medium |

Deposit Comparison

The amines and sulfuric acid can form salt or complex in crude phenol by reaction. If the complex doesn't have good solubility in crude phenol, they can separate from the liquid phase, which may cause fouling in phenol production system. The deposit contents of different amines are compared in order to select the amines which have lower deposition or foulants.

300 ppm different amines were separately added in crude phenol samples containing 300 ppm $H_2SO_4$. Some samples like AEEA, DETA, HMDA, TEPA and HPA-X are not very transparent and others are clear. The small particles in turbid samples may precipitate in the bottom after standing for a while.

The crude samples were centrifuged to separate the deposition from the solution. Firstly, the sediments were heated in vacuum oven at 40-50° C. overnight to remove residue phenol and acetone after washing. The deposition contents of different samples were weighed. No deposition was detected with TETA, MPMD, MEA, AEP, DEA and MIPA. Other amines including HMDA and DETA show deposition in crude phenol. The weight of DETA deposition is only one fourth of HMDA's.

The deposition content of the comparable and inventive examples is summarized in Table 3. The inventive examples like EDA, TETA, DETA, AEEA, HPA-X, TEPA and AEP show higher neutralization efficiency than comparable examples like HMDA and MPMD.

TABLE 3

The Deposition Contents of Different Amines

| Examples | Neutralizing Agent | Deposition % | Fouling Risk |
|---|---|---|---|
| Comparable example | HMDA | 0.26 | High |
| Comparable example | MPMD | 0 | Low |
| Comparable example | MEA | 0 | Low |
| Comparable example | MIPA | 0 | Low |
| Comparable example | NMEA | 0 | Low |
| Comparable example | DEA | 0 | Low |
| Inventive example | EDA | 0.01 | Low |
| Inventive example | DETA | 0.07 | Low |
| Inventive example | TETA | 0 | Low |
| Inventive example | AEEA | 0.03 | Low |
| Inventive example | HPA-X | 1.05 | High |
| Inventive example | TEPA | 0.98 | High |
| Inventive example | AEP | 0 | Low |

4. Conclusion

Considering both neutralization efficiency and fouling risk, the inventive examples EDA, DETA, TETA, AEEA and AEP have better performance than comparable examples like HMDA and MPMD.

What is claimed is:

1. A method for the production of phenol, the method comprising:
   (a) synthesizing phenol through a process that utilizes an acidic catalyst;
   (b) neutralizing the acidic catalyst after substantial completion of step (a) by addition thereto of a neutralization composition,
   wherein the neutralization composition comprises an ethyleneamine derivative, and wherein the neutralization composition is substantially free of amine compounds other than ethyleneamine derivatives, and wherein the ethyleneamine derivative is selected from the group consisting of: ethylenediamine (EDA), diethylenetriamine (DETA), triethylenetetramine (TETA) aminoethylpiperazine (AEP), tetraethylenepentamine (TEPA), and mixtures of two or more thereof,
   and wherein the ethyleneamine derivative is selected from the group further consisting of heavy polyamine X (HPA X), wherein HPA X is a complex mixture of linear, branched, and cyclic ethyleneamines having six or more nitrogen atoms per molecule and having a molecular weight of 275.

* * * * *